(12) United States Patent
Sinden et al.

(10) Patent No.: US 8,932,577 B2
(45) Date of Patent: Jan. 13, 2015

(54) TREATMENT OF LIMB ISCHEMIA

(75) Inventors: John Sinden, Guildford (GB); Erik Miljan, Guildford (GB); Paolo Madeddu, Bristol (GB)

(73) Assignee: Reneuron Limited, Surrey (GB)

( * ) Notice: Subject to any disclaimer, the term of this patent is extended or adjusted under 35 U.S.C. 154(b) by 0 days.

(21) Appl. No.: 13/141,453

(22) PCT Filed: Feb. 5, 2010

(86) PCT No.: PCT/GB2010/050185
§ 371 (c)(1),
(2), (4) Date: Dec. 21, 2011

(87) PCT Pub. No.: WO2010/089605
PCT Pub. Date: Aug. 12, 2010

(65) Prior Publication Data
US 2012/0093786 A1  Apr. 19, 2012

(30) Foreign Application Priority Data
Feb. 6, 2009 (GB) .................................. 0902034.8

(51) Int. Cl.
  *A61K 35/00* (2006.01)
  *A61P 9/00* (2006.01)
  *A61P 9/10* (2006.01)
  *C12N 5/0797* (2010.01)
  *A61K 35/12* (2006.01)

(52) U.S. Cl.
  CPC ............... *C12N 5/0623* (2013.01); *A61K 35/12* (2013.01); *C12N 2510/04* (2013.01)
  USPC ..................................... 424/93.21; 424/93.7

(58) Field of Classification Search
  CPC .................................................. C12N 5/0623
  See application file for complete search history.

(56) References Cited

U.S. PATENT DOCUMENTS

| | | | |
|---|---|---|---|
| 6,399,384 B1 | 6/2002 | Jat | |
| 6,465,215 B1 | 10/2002 | Price et al. | |
| 6,569,421 B2 | 5/2003 | Hodges | |
| 6,852,533 B1 | 2/2005 | Rafii et al. | |
| 7,048,921 B2 | 5/2006 | Sinden et al. | |
| 7,247,298 B2 | 7/2007 | Hodges | |
| 7,371,374 B2 | 5/2008 | Sinden et al. | |
| 7,416,888 B2 | 8/2008 | Sinden et al. | |
| 7,419,827 B2 | 9/2008 | Sinden et al. | |
| 7,666,672 B2 | 2/2010 | Sinden et al. | |
| 2005/0069527 A1 | 3/2005 | Laughlin et al. | |
| 2005/0142659 A1* | 6/2005 | Rafii et al. | 435/366 |
| 2006/0067918 A1* | 3/2006 | Sinden et al. | 424/93.7 |
| 2006/0104959 A1 | 5/2006 | Sinden et al. | |
| 2008/0118479 A1 | 5/2008 | Sinden et al. | |
| 2012/0076854 A1 | 3/2012 | Hope et al. | |
| 2013/0171177 A1 | 7/2013 | Corteling et al. | |

FOREIGN PATENT DOCUMENTS

| | | |
|---|---|---|
| EP | 1 645 626 A1 | 4/2006 |
| JP | 2002-171965 | 6/2002 |
| JP | 2005-287430 | 10/2005 |
| JP | 2006-238875 | 9/2006 |
| WO | WO 99/11758 A2 | 3/1999 |
| WO | WO 00/18414 A1 | 4/2000 |
| WO | WO 00/50568 | 8/2000 |
| WO | WO 03/035879 | 5/2003 |
| WO | WO 03/059276 A2 | 7/2003 |
| WO | WO 2005/026201 | 3/2005 |
| WO | WO 2006/032876 | 3/2006 |
| WO | WO 2006/055685 A2 | 5/2006 |
| WO | WO 2006/130433 A2 | 12/2006 |
| WO | WO 2007/013771 A1 | 2/2007 |
| WO | WO 2007/052036 | 5/2007 |
| WO | WO 2009/020201 A1 | 2/2009 |
| WO | WO 2010/064054 | 6/2010 |
| WO | WO 2010/089605 A1 | 8/2010 |
| WO | WO 2012/004611 | 1/2012 |

OTHER PUBLICATIONS

Alessandri, G. et al. "Genetically Engineered Stem Cell Therapy for Tissue Regeneration" *Ann. N. Y. Acad. Sci.*, 2004, 1015:271-284.
Ford, M,C, et al. "A macroporous hydrogel for the coculture of neural progenitor and endothelial cells to form functional vascular networks in vivo" *PNAS*, Feb. 2006, 103(8):2512-2517.
Gray, B.H. et al. "Atherosclerotic Peripheral Vascular Disease Symposium II Lower-Extremity Revascularization: State of the Art" *Circulation*, Dec. 2008, 118:2864-2872.
Katare, R. etal. "Injection of human neural stem cell line in a mouse hind limb ischemia model promotes muscle neovascularisation" *AHA Scientific Sessions*, Nov. 2009, 2 pages.
Katare, R. et al. "Injection of a human neural stem cell line promotes muscle neovascularisation in a diabetic hind limb ischemia mouse model" *UK Diabetes: Annual Professional Conference*, Mar. 2010, 1 page.
Keller, L.H. "Bone Marrow-Derived Aldehyde Dehydrogenase-Bright Stem and Progenitor Cells for Ischemic Repair" *Spotlight on Heart Failure Translational Research*, 2009, 202-206.
Madeddu, P. et al. "Injection of hNSC line in a mouse hindlimb ischemia model promotes muscle neovascularisation" *AHA Scientific Sessions*, Nov. 2009, 1 page.
Nolden, L. etal. "Humane embryonale Stammzellen" *Bundesgesundheitsbl-Gesundheitsforsch-Gesundheitsschutz*, 2008, 51:1026-1032.
Pollock, K. et al. "A conditionally immortal clonal stem cell line from human cortical neuroepithelium for the treatment of ischemic stroke" *Experimental Neurology*, 2006, 199:143-155.
Sprengers, R.W. et al. "Progenitor Cell Therapy in Patients With Critical Limb Ischemia Without Surgical Options" *Ann. Surg.*, Mar. 2008, 247(3):411-420.
Brazelton TR et al., "From Marrow to Brain: Expression of Neuronal Phenotypes in Adult Mice" *Science*, 2000, 290:1775-1779.
Hodges H et al., "Making Stem Cell Lines Suitable for Transplantation" *Cell Transplantation*, 2007, 16:101-115.

* cited by examiner

*Primary Examiner* — Scott Long
(74) *Attorney, Agent, or Firm* — Saliwanchik, Lloyd & Eisenschenk

(57) ABSTRACT

The present invention uses neural stem cells in the manufacture of a medicament for the treatment of a patient suffering peripheral arterial disease. The invention is particularly suited for treating limb ischemia or Buerger's disease.

8 Claims, 6 Drawing Sheets

TREATMENT OF LIMB ISCHEMIA

CROSS-REFERENCE TO RELATED APPLICATION

This application is the U.S. national stage application of International Patent Application No. PCT/GB2010/050185, filed Feb. 5, 2010, the disclosure of which is hereby incorporated by reference in its entirety, including all figures, tables and amino acid or nucleic acid sequences.

FIELD OF THE INVENTION

The present invention relates to cell therapies for the treatment of peripheral arterial diseases, including but not limited to: acute and chronic critical limb ischemia, Buerger's disease and critical limb ischemia in diabetes.

BACKGROUND OF THE INVENTION

Lower extremity peripheral arterial occlusive disease poses a unique challenge to traditional endovascular therapies. The diffuse nature of lower extremity atherosclerotic disease, the presence of chronic total occlusions, poor distal runoff, and the presence of limb ischemia have contributed to disappointing results in treatment. Peripheral arterial disease (PAD) affects ~12 million people in the United States and approximately 220,000 to 240,000 amputations occur yearly in the US and Europe. PAD encompasses chronic limb ischemia, which progresses into critical limb ischemia leading to the distal limb at risk of amputation, and acute limb ischemia, with a rapid loss of blood flow damaging tissue within hours. Critical Limb ischemia (CLI) is often associated with diabetes, resulting in compromised vasculature and exaggerated tissue damage. A separate chronic condition, Buerger's Disease, compromises blood flow to the hands and feet resulting in the loss of fingers and toes. Chronic PAD generally results in poor wound healing, ulcers and tissue necrosis in limbs and extremities that may result in loss of the affected limb as a result of non-traumatic amputation.

In CLI, patients present with chronic ischemic rest pain, presence of tissue ulcers, or gangrene as a result of reduced blood flow due to proven occlusive disease. The condition is the progression of PAD as diagnosed by a low or a lack of pulse in the foot, low ankle brachial index (ABI, blood pressure in ankle/blood pressure in arm <0.6) reduced blood pressure in toe (<30-50 mm Hg), reduced transcutaneous oxygen (<30-50 mm Hg). Occlusion of arteries is usually caused by atherosclerosis within large communicating arteries that is confirmed using angiography or duplex ultrasound scanning. Once diagnosed with critical limb ischemia, patients have a risk of limb loss of 10 to 40% over the first year. CLI patients are usually also at risk for myocardial infarction, stroke and coronary artery disease.

PAD is a common cardiovascular complication in patients with diabetes. In contrast to peripheral arterial disease in non-diabetic individuals, it is more prevalent and, because of the distal territory of vessel involvement and its association with peripheral neuropathy, it is more commonly asymptomatic. It is estimated that approximately 20% of patients with symptomatic PAD are diabetic. Diabetics with limb ischemia are at a greater risk of tissue damage. The pain felt by non-diabetics while walking, ie the first indication of limb ischemia, may not be perceived by diabetics due to the presence of peripheral neuropathy. Diabetic patients may note pain in the thighs and buttocks while walking due to the loss of reserve blood flow or have a sensation of the muscles being tired.

Patients with mild cases of limb ischemia are treated medically with antiplatelet (clopidogrel) and vasodilator therapy (pentoxifylline). Risk modification is also used to eliminate smoking and control hypertension, which are contributing factors to PAD. Monitored exercise regimens are the most effective treatment of PAD with sessions lasting longer than 30 minutes at least three times per week, with programs lasting at least six months (Gey et al 2004).

Patients with moderate limb ischemia, moderate to severe claudication and walking distances of 200 meters or less are candidates for percutaneous transluminal angioplasty along with medical therapy (Gray et al 2008). Patients with severe symptoms including ischemic rest pain and chronic ulcers are candidates for angioplasty with and without stent insertion and/or bypass surgery. Unfortunately, surgical procedures that restore blood flow commonly result in the loss of patency of the vessels over one to two years with up to 20% of patients having re-stenosis of the affected arteries. Complications also arise in up to 25% of patients having poor healing at the wound site.

Approximately 20 to 30% of patients with the most severe symptoms of CLI are not considered candidates for vascular or endovascular procedures and are, therefore, considered for amputation. Patients with necrotic tissue and wet or dry gangrene are normally considered candidates for amputation, although some cases of dry amputation resolve with the affected tissue being shed. Amputation is also considered in cases of advanced ischemia associated with a low ankle brachial index value (<0.3).

Acute limb ischemia (ALI) is defined as any sudden decrease or worsening in limb perfusion (Gray et al 2008). The causes of ALI are usually an acute thrombotic occlusion of a pre-existing stenotic arterial segment (60% of cases) or an embolus (clot) usually originating from the heart or from a segment of an atherosclerotic plaque (30% of cases) stopping blood flow in a peripheral artery. Blockages also occur from trauma, fractures, blunt and penetrating injuries and from complications of surgical procedures. Damage from ALI occurs in the affected muscles within hours of onset.

Patients with ALI present with a generalised set of symptoms resulting from loss of blood flow to the limb. These symptoms include; Pain, Pallor (whiteness in the limb), Pulseless extremity, Poikolothermia (limb assumes surrounding temperature), Parasthesia (tingling sensation) and Paralysis. As the period of ALI lengthens the limb starts to have a mottled appearance as blood begins to coagulate. The presence of anesthesia, with the patient unable to feel touch in the limb, and being unable to wiggle the toes or fingers are the key to diagnosing complete ischemia, requiring emergency surgical treatment (Callum & Bradbury 2000).

Prompt treatment of ALI is necessary as a few hours of resolution can make the difference between limb amputation (and possible death) and recovery of limb function. Heparin administration is usually the first line of treatment to limit propagation of a thrombus and protect the collateral circulation of the affected limb (Gray et al 2008). Patients with limbs that are viable or with a marginal threat (no or minimal sensory loss and audible venous signals) are usually treated with catheter-directed thrombolytic therapy. Cases with an immediate threat of damage (pain, muscle weakness and inaudible arterial signals) may be treated using thrombolytic therapy, a percutaneous thrombectomy device or surgical bypass. Patients presenting with non-viable limbs having irreversible damage (loss of sensation, paralysis with muscle rigor and inaudible arterial and venous signals) face amputation of the limb.

Patients with ALI still face risk of secondary damage to the limb after restoration of blood flow due to reperfusion injury. Tissue suffers from peroxidation and neutrophil invasion along with swelling of the limb. Peripheral nerve injury suffered from the ischemic period and resulting reperfusion may lead to chronic pain. Stress in the peripheral organs from products in the blood as a result of the ischemic episode can lead to damage and organ failure. Patients suffering from coronary artery disease have increased risk of death after ALI.

There are approximately 200,000 cases of ALI in the US every year. Of those cases 10 to 20% of cases have in-hospital mortality due to heart failure and or recurrent embolism.

There is also an angiogenic response to ischemia. Ischemia-induced angiogenesis involves the growth of new microvasculature and capillary beds. Cells within the ischemic tissue respond to hypoxia (low oxygen levels) and induce angiogenesis through the hypoxia-inducible factor 1 (HIF-1).

Disease states related to reductions in vascular perfusion may be treated using strategies that promote re-vascularisation of tissue. Most approaches for promotion of vascularisation have centred on delivery of a gene or growth factor, typically VEGF and/or fibroblast growth factor (FGF). Although clinical trials for angiogenic therapy have been shown to alleviate secondary symptoms, they have failed to demonstrate improvements in exercise performance, the US FDA primary endpoint for approval of an angiogenic agent. Some side-effects have been associated with the administration of VEGF and FGF including hypotension, edema, renal insufficiency and vascular leakage.

Angiogenesis stimulated by VEGF exposure does not consistently form stable functional vasculature. Long term exposure to VEGF is required to produce stable microvasculature that does not degrade after withdrawal of the VEGF stimulus. Concentrations of VEGF are also critical as low dosages of VEGF result in vessels with increased permeability leading to oedema and high doses of VEGF can result in formation of hemangioma and vascular leakage.

Implantation of dissolvable matrices embedded with growth factors may be used as a source for growth factors. Growth factors (FGF and VEGF) may be incorporated into a biodegradable scaffolds (for example, PLGA based) that is slowly released as the matrix degrades. Such an approach allows a timed release of growth factors delivered locally to the site of interest. Once the new vasculature is established, growth factors may be administered in a controlled fashion to maintain optimal functionality of the new vessels.

Cell-based therapies have also been proposed. Endothelial progenitor cells (EPC) originating in the bone marrow play a significant role in endogenous neovascularisation of injured vessels. EPC transplantation has been shown to induce new vessel formation in ischemic myocardium and hind limb, and to accelerate re-endothelialisation of injured vessels and prosthetic vascular grafts in humans and in various animals models. EPCs have been demonstrated as a potential therapy for a cell based strategy for the rescue and repair of ischemic tissues and injured blood vessels. EPCs are thought to originate from a multiple precursors in the bone marrow. The cells have a high proliferative potential albeit with a finite number of cell divisions. Numbers of EPCs are low under normal conditions, however, stimulation with exogenous cytokines and hormone raises the number of EPCs several fold. The mechanisms governing the mobilisation, homing and differentiation of EPCs in vivo remain largely unknown. EPCs can be isolated from peripheral blood and expanded to provide sufficient numbers for autologous transplantation.

Numbers of EPCs are reduced in patients with significant risk of cardiovascular disease. In patients with severe coronary artery disease, the potency of EPCs as defined by colony-forming capacity and migratory activity was markedly reduced and associated with reduced neovascularisation in hind limb ischemia (Heeschen et al 2004). Similarly, numbers of EPCs are reduced in patients with type I or type II diabetes. The ability of EPCs to induce angiogenesis in vitro is also reduced. The reduction of the numbers of EPCs and of their activity suggest that their deficits are involved with some of the vascular complications associated with diabetes, such as endothelial dysfunction, that predispose patients to diffuse atherosclerosis and impaired neovascularisation after ischemic events.

The implantation of EPC progenitor cells into the ischemic limb has been shown to promote new vessel formation (neoangiogenesis) in the affected limb. Administration of bone marrow cells into a mouse model of hind-limb ischemia was the first observation that cell therapy can contribute to neoangiogenesis following an ischemic insult (Asahara et al 1999). In 2002, Tateishi-Yuyama et al. first reported that autologous bone marrow mononuclear cell implantation was an effective treatment for patients with ischemic limbs due to peripheral arterial disease (Tateishi-Yuyama et al 2002). In additional studies, the optimal dose of autologous bone marrow derived cells for the treatment of limb ischemia was reported to be no less than $1\times10^5$ cells, and the optimal implantation dose was $1\times10^8$ cells (Gu et al 2006; Liao & Zhao 2008).

Functional studies monitoring treadmill running in rats with hind limb ischemia has shown increases in both perfusion of the limb and in performance of treated animals. Bone marrow administration has also increased angiogenesis in diabetic rats with hind limb ischemia.

A number of variations of treatment with bone marrow cell populations into the muscle of ischemic hind limb have demonstrated a promotion of angiogenesis via the generation of angiogenic factors and by promotion of endothelial progenitor cells.

The feasibility of cell implantation using autologous bone marrow derived cells including hematopoietic, endothelial and mesenchymal stem cells or their combinations has been demonstrated in a number of clinical studies, with varying levels of benefit being observed. While overall positive results have been observed, the limitations are clear: for older and diabetic patients, the therapeutic potential of the patients' own cells is diminished. In addition, the inconvenience and cost of extraction, isolation, purification, release testing and readministration of patient specific stem cells is a hindrance to widespread reimbursable medical application.

Real clinical and industrial progress in cell implantation for the treatment of peripheral ischemia in all its manifestations requires a stem cell product which is able to meet all the desired characteristics:

High therapeutic effectiveness
Excellent safety profile
Standardised for all patients (i.e., not patient specific)
Available on demand, even in emergency situations.
Low cost of goods (compared to patient-specific treatments)

There is therefore a clear need for improved treatments for peripheral arterial disease, including limb ischemia.

SUMMARY OF THE INVENTION

The present invention is based on the development of cell lines that have favourable characteristics making them useful in treating peripheral arterial disease.

According to a first aspect of the present invention, pluripotent neuroepithelial cells are used in the manufacture of a medicament for the treatment of a disorder associated with peripheral arterial disease.

According to a second aspect, there is a method for treating peripheral arterial disease in a patient comprising administrating to the patient a therapeutic dose of neural stem cells.

According to a third aspect, neural stem cells are for use in the treatment of a patient suffering peripheral arterial disease.

The cells are particularly suitable for the treatment of limb ischemia.

DESCRIPTION OF THE DRAWINGS

The present invention is described with reference to the accompanying drawings wherein.

DETAILED DESCRIPTION OF THE INVENTION

Figure 1:
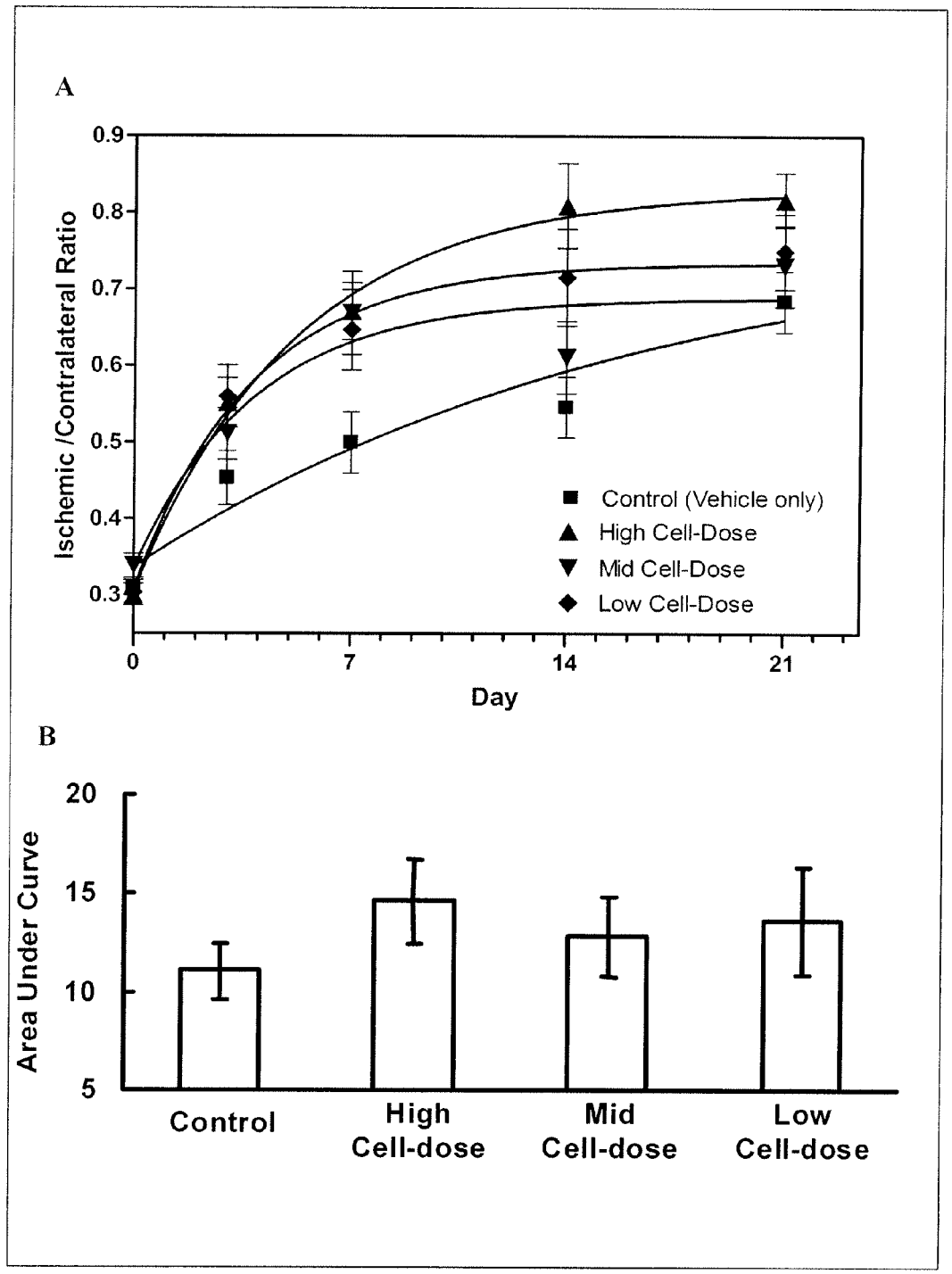
FIG. 1A) is a line graph showing that neural stem cell treated ischemic limb has an increased and sustained blood flow when compared to the vehicle only treated ischemic limb. Blood flow measurements where made using laser Doppler on days 0, 3, 7, 14 and 21. Data is expressed as average ratio of blood flow measured within the ischemic limb over the non-ischemic (contralateral) limb. B) is a histogram that graphs the area under each curve in that is shown in A). B) shows the overall improvement over the course of the study in the cell treated ischemic limb compared to vehicle only treated ischemic limb.

The present invention is based on the surprising discovery that an alternative somatic stem cell type to cells of bone marrow and mesenchymal origin, namely neural stem cells, provide a scalable, safe and very potent allogenic treatment for peripheral arterial disease.

Neural stem cells (NSCs) can be derived from the ventricular and hippocampal regions of the fetal and adult brain and can be isolated by sorting brain cells using specific cell surface markers (Uchida et al., 2000) and expanded in defined media with additional growth factors (Reynolds and Weiss, 1992; Carpenter et al., 1999; Vescovi et al., 1999). NSCs can also be generated from pluripotent cells directly, such as embryonic stem cells (Conti et al. 2005). Although such cells are suitable, the capacity for expansion of NSCs is limited to a relatively small number of cell passages, necessitating additional technologies to permit a scalable, standardised, stable and, therefore, commercial application. The cells may therefore be modified to permit multiple cell passages or may be cultured under conditions which promote multiple cell passaging. Suitable conditions will be apparent to the skilled person.

As used herein, the term "neural stem cells" has its usual meaning in the art and refers to cells which have the capacity to differentiate into cells with different neural phenotypes. The cells are lineage-restricted and maybe pluripotent, multipotent or oligopotent. The term also includes cells referred to as "progenitor" cells.

The term "pluripotent" is well recognised in the art and refers to the ability of the cells to develop into more than two types of cells. Pluripotent neuroepithelial cells are capable of differentiating into neural cells of a different phenotype.

The term "progenitor" is well recognised in the art and refers to the ability of the cells to differentiate into a defined phenotype. Neural progenitor cells can only differentiate into cells with a neural phenotype.

The neural stem cells of the invention may be derived from a fetal or adult source. The cells may also be derived originally from embryonic stem cells, which have been induced to undergo differentiation into neural stem cells. The cells may also be induced pluripotent cells, i.e. genetically reprogrammed cells which, through the use of transcription factors, have been induced into a pluripotent phenotype.

In one embodiment, the cells may have a conditionally-inducible oncogene present. The term "conditionally-inducible" is used herein to refer to oncogenes, the expression of which can be regulated under certain conditions. The oncogene will undergo expression when so-called permissive conditions are applied. For example, some oncogenes are temperature-sensitive and are only expressed when the temperature of their environment is below a certain value. The oncogenes can therefore be switched from an "oncogenic state" to a "non-oncogenic state" by regulatory conditions. In one embodiment of the invention, the oncogene that is used is a non-DNA binding, temperature-sensitive, mutant of the SV 40 large T-antigen gene (U19tsA58). Suitable alternatives are also known and include the oncogene of the polyoma T-antigen.

Genetic transgene expression of c-myc, a naturally occurring protooncogene that is normally expressed during cell development, is a means of stably enhancing cell proliferation and preventing changes in cell karyotype during large-scale expansion required to manufacture a cell line. For the therapeutic use of the myc-immortalised cells, a preferred embodiment would permit the control over the function of the Myc protein. The approach to dealing with scalability, safety and stability in the manufacture of neural stem cells for therapy is to generate clonal cell lines by genetic modification of passage 0-1 neural stem cells under quality assured conditions. The technology (c-mycER$^{TAM}$) employed to achieve conditional growth control is a fusion protein comprising a growth promoting gene, c-myc, and a hormone receptor that is regulated by a synthetic drug, 4-hydroxy-tamoxifen (4-OHT) (Littlewood et al., 1995). In a preferred embodiment, the cell line used is that described as CTX0E03 in European Patent Application No. 05255932.5. The CTX0E03 line is not a prototype but a 'clinical-grade' cell line which has undergone cGMP cell manufacture and has been approved by the U.K. competent authority (Medicines and Healthcare Regulatory Authority) for a Phase I clinical trial in the UK in stroke.

As used herein, the term "peripheral arterial disease" or "PAD" refers to acute and chronic critical limb ischemia, Buerger's disease and critical limb ischemia in diabetes.

As used herein, the term 'patient' refers to a mammal including a non-primate (e.g. a cow, pig, horse, dog, cat, rat and mouse) and primate (e.g. a monkey and human), and more preferably a human.

The present invention provides a medicament, comprising of neural stem cells (or progenitor cells) for the therapeutic treatment of patients with peripheral arterial disease.

Methods for the preparation of formulations for delivery to a patient will be apparent to the skilled person. Suitable excipients, diluents etc., will again be apparent based on current practice in preparing neural stem cell-based therapies and described in the literature. The amount of cells required for delivery will vary depending on the form of treatment, the severity of the disease/damage, and the need for applying multiple doses over a treatment period. However, the skilled person can readily determine the appropriate treatment based on existing cell transplantation therapies.

In a preferred embodiment, the cells for transplantation are suspended in a composition comprising Trolox, $Na^+$, $K^+$, $Ca^{2+}$, $mg^{2+}$, $Cl^-$, $H_2PO_4^-$, HEPES, lactobionate, sucrose, mannitol, glucose, dextron-40, adenosine and glutathione. The composition preferably does not include a dipolar aprotic solvent, e.g. DMSO. Suitable compositions are available commercially, e.g. HypoThermosol®-FRS.

Such compositions are preferred as they allow the cells to be stored at 4° C. to 25° C. for extended periods (hours to days) or preserved at cryothermic temperatures, i.e. temperatures below −20° C. The cells can then be administered in this composition, without the need to remove DMSO or other toxic compounds.

The route of administration of the said cells to the patient may be via intravenous or intramuscular injection. The cell dose will depend on the extent and severity of the ischemia but a preferred range is from $5\times10^4$ to $5\times10^8$ cells per dose.

Accordingly, in an embodiment of the invention, the cells are capable of expansion within the tissue culture laboratory such that the numbers of cells obtained is sufficient to treat more than one patient and, in the preferred embodiment, shall be capable of cell banking.

Neural stem cells or progenitor cells are suitable for the said treatment, with the preferred embodiment using human neural stem cells (hNSCs). The method of the invention is based upon the surprising finding that hNSCs provide an effective treatment for peripheral arterial disease. hNSCs may be derived from a variety of sources, including but not limited to:

i) fetal or adult central nervous system (e.g. brain and spinal cord);
ii) fetal or adult tissue containing peripheral nervous system;
iii) differentiation of human embryonic stem cells into a hNSC phenotype; and
iv) differentiation of induced pluripotent human stem (iPS) cells into a hNSC phenoytpe.

The cells used in the invention will increase blood supply to an ischemic tissue. In a preferred embodiment, a therapeutic increase in blood supply is a result of an increase in blood vessel formation (angiogenesis) following implantation of the said cells. The method of this invention provides cells that are pro-angiogenic following transplantation.

The invention will now be described by reference to the following non-limiting example.

Method
Preparation of Cells for Implantation

The derivation of stable human neural stem cell lines immortalised with the c-mycER transgene has been previously described (U.S. Pat. No. 7,416,888; Miljan et al 2008; Pollock et al 2006). The method described herein uses a human neural stem cell line conditionally immortalised with the c-mycER transgene, referred to as CTX0E03 cells with ECACC Accession No. 04091601 or derivatives thereof.

Initial experiments used cultures of cells that were expanded in T-flasks until 70% to 90% confluent. The spent medium was aspirated and then the cell monolayer washed with HBSS without magnesium or calcium ions (Invitrogen). The wash was aspirated and then the cells dissociated with recombinant bovine trypsin (Lonza TrypZean/EDTA) for 5 min at 37° C. The dissociated cell suspension was mixed with a trypsin inhibitor solution (0.55 mg/ml soybean trypsin inhibitor [Sigma], 1% HSA [Grifols], 25 U/ml benzon nuclease [VWR] in DMEM:F12 [Invitrogen]) and centrifuged for 5 min at ~500×g. The supernatant was aspirated and the cell pellet washed in 50% HypoThermosol®-FRS (BioLife Solutions) in DMEM:F12 followed by centrifugation at ~500×g for 5 min. The cell pellet was then suspended in HypoThermosol®-FRS at a concentration of 10,000 cells per microliter (low-dose), 33,000 cells per microliter (mid-dose) and 100,000 cells per microliter (high-dose). Ten aliquots containing 45 microliters of cell suspension was prepared at each concentration. The cell suspension aliquots were assigned a 24 hr shelf-life and are referred to herein as fresh cell suspensions. Ten aliquots containing 45 microliters of HypoThermosol®-FRS were prepared containing no cells to be used for control injections.

In subsequent experiments, a fully manufactured "ready-to-inject" cryopreserved cell suspension formulation was investigated. This manufacturing process used triple layer T-Flasks [Nunc] to expand cultures of cells. To passage, spent medium was decanted from the triple layer T-flasks and recombinant bovine trypsin (Lonza TrypZean/EDTA) dissociation reagent was added for 5 min to 180 min at 37° C., with no preceding wash. The dissociated cell suspension was mixed with a trypsin inhibitor solution (0.55 mg/ml soybean trypsin inhibitor [Sigma], 1% HSA [Grifols], 25 U/ml benzon nuclease [VWR] in DMEM:F12 [Invitrogen]) and this cell suspension was added directly to multiple triple layer T-Flasks containing fresh culture medium using a split ratio in the range of 1:2 to 1:4, with no centrifugation. A full medium change was performed the following day. The final formulation of the cell suspension from the triple layer T-flasks required centrifugation of the dissociated cell suspension, as described in the preceding paragraph. The cell pellet was then suspended in HypoThermosol®-FRS at a concentration of 50,000 cells per microliter and cryopreserved for frozen storage. This scaled up triple layer T-flask manufacturing represents an advantage over single layer T-flask expansion as washing and centrifugation steps were omitted. The cryopreserved formulation of the cell suspension is advantageous because it can be stored in a frozen state for long periods of time and defrosted and directly injected with no further manipulation, on demand.

Mouse Hind Limb Ischemia Model

All animal work was performed in accordance with the UK Animals (Scientific Procedures) Act (1986) and approved by the local animal Ethical Review Committee. Immunodeficient ICRF NUDE Nu/Nu-mice (Harlan) were housed for 7 days prior to the hind limb ischemia surgery. Mice were anesthetized with 2,2,2-tribromoethanol (Avertin) and the left femoral artery exposed. The exposed femoral artery was separated from the femoral vein as proximal as possible using fine forceps. The femoral artery was then ligated at both proximal and distal sites using 6-0 silk suture, followed by electrical cauterization of the artery between the sutured points. During the same procedure, three 10 microliter injections (total injection volume of 30 microliter per animal) of the cell suspensions or vehicle (control) were performed at three different sites into the ischemic adductor muscle using a fine needle (30 gauge) disposable syringe. The wound was then closed using 6-0 suture and monitored until recovery. In the first experiment, a total of 10 animals were used for each treatment group (i.e. 40 animals used in the entire study), consisting of: i) control (vehicle only); ii) fresh cells High-Dose (total $3\times10^6$ cells implanted per animal); iii) fresh cells Mid-Dose (total of $1\times10^6$ cells implanted per animal); and iv) fresh cells Low-Dose (total of $0.3\times10^6$ implanted per animal). In a second experiment, the performance of the freshly prepared cell suspension was directly compared to the cryopreserved cell suspension. A total of 10 animals were used for each treatment group (ie. 80 animals used in the entire study), consisting of: i) fresh control (vehicle only); ii) fresh cells (total $3\times10^3$ cells implanted per animal); iii) fresh cells (total of $3\times10^4$ cells implanted per animal); iv) fresh cells (total of $3\times10^5$ implanted per animal); v) frozen control (vehicle only); vi) cryopreserved cells (total $3\times10^3$ cells implanted per animal); vii) cryopreserved cells (total of $3\times10^4$ cells implanted per animal); iix) cryopreserved fresh cells (total of $3\times10^5$ implanted per animal The surgeon remained blinded to the treatments animals received throughout the course of the study and analysis.

A third experiment was conducted to investigate implantation of cells using the hind limb ischemia model in an immune competent mouse with diabetes. Diabetes was induced in wild-type CD1 mice by streptozocin injection (40 mg/g/day×5 days) 4 weeks prior to performing unilateral limb ischemia, as described for the immunodeficient ICRF NUDE Nu/Nu-mice used in the first two experiments. At the time of ligation, three different doses of cryopreserved cells or vehicle (control) were administered by injection into the ischemic limb adductor muscle. A total of 10 animals, confirmed to develop diabetes, were used for each treatment group (ie. 40 animals used in the entire study), consisting of: i) control (vehicle only); ii) cryopreserved cells (total $3\times10^4$ cells implanted per animal); iii) cryopreserved cells (total of $3\times10^5$ cells implanted per animal); iv) cryopreserved cells (total of $1.5\times10^6$ implanted per animal). Doppler measurements were taken days 3, 7, 14 and 21. Blood flow measurements, tissue partial oxygen pressure (Oxford Optronix) and capillary density of the treated ischemic adductor muscle were taken on day 21.

Clinical Outcome from Ischemia

The hind-limb was measured by laser Doppler following the surgery. This is the day 0 Doppler. Follow-up Doppler measurements were made on all animals on Days 3, 7, 14 and 21 post-surgery. Doppler measurements were carried out on the animal anesthetized with 2,2,2-tribromoethanol (Avertin), followed by recover of the animal on a warming pad and incubator until fully recovered. The ratio of perfusion between ischemic to non-ischemic foot was calculated. The cell treated ischemic limbs showed an increased perfusion over the control vehicle only treated ischemic limbs (FIG. 1). The improved perfusion of the cell treated ischemic limb was maintained throughout the course of the study. Spontaneous recovery of the control non-cell treated ischemic limb is noted by laser Doppler, however, the rate of recovery observed in the cell-treated ischemic limb is faster than without cell-treatment. It is important to note that the laser Doppler measurements are advantageous in that they can be made in living animals but the penetration of the laser and depth of measurement is limited.

Figure 2:
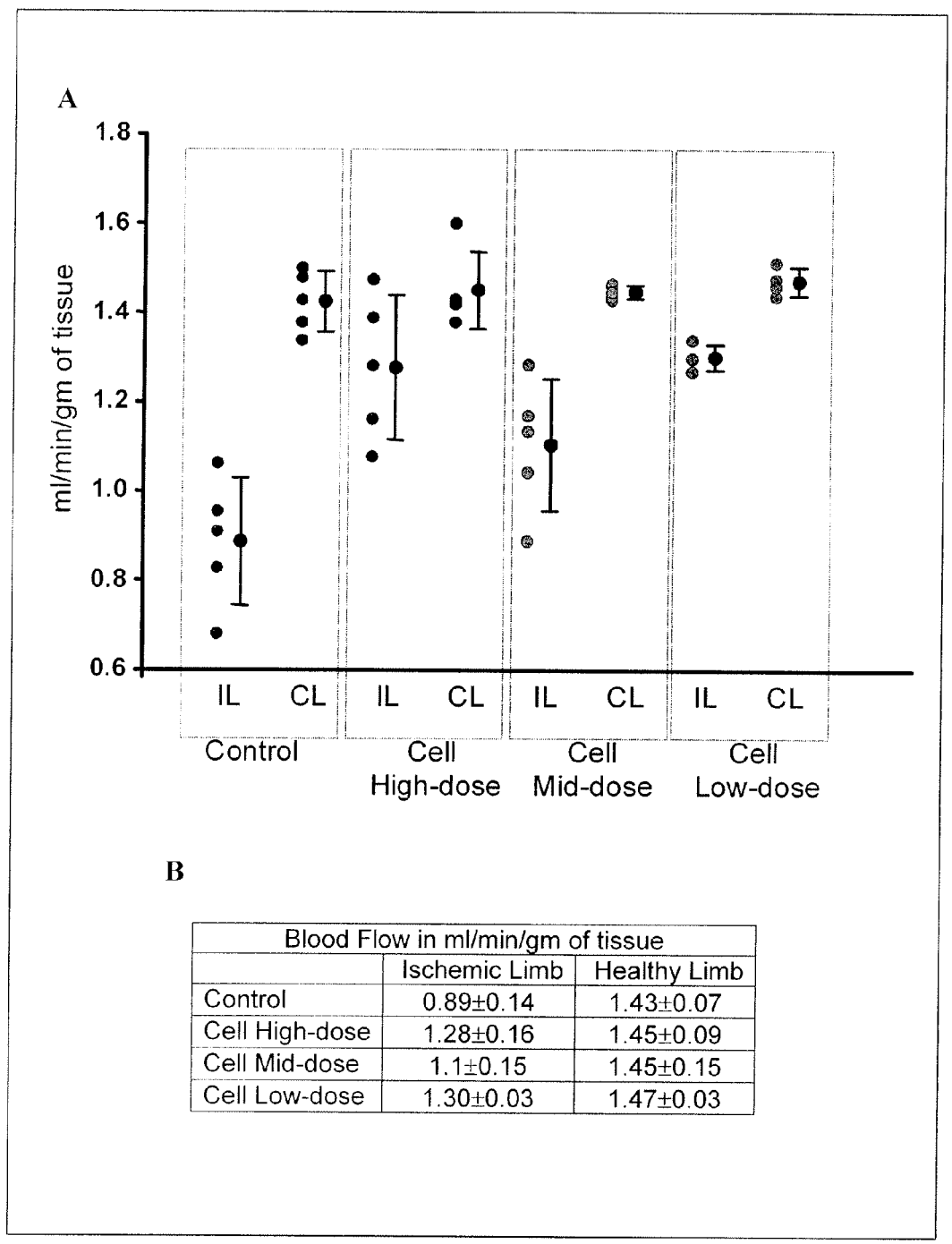
FIG. 2A) is a scatter plot showing that neural stem cell treated limb muscle has an increase in blood flow (ml/min/gram of tissue) compared to the vehicle only treated ischemic limb muscle at 21 days. Animals were perfused with fluorescent microspheres intravenously at the end of the 21 day study and the amount of fluorescent microspheres present in the ischemic limb (IL) and contralateral (CL) limb muscle tissue was measured. The amount of fluorescent microspheres present within the limb muscle tissue directly correlates with the amount of blood flow within the affected limb. B) Average blood flow data represented shown in A) in numerical table format.

Upon completion of the study at day 21, absolute blood flow measurements through the entire adductor muscle were carried out using fluorescent microspheres. Five animals from each group underwent this procedure. Under anaesthesia, fluorescent microspheres (Invitrogen 0.02 μm in diameter) were injection in to left ventricle of the heart in five intervals of 10 seconds. After the final injection, the reference blood sample is taken, the animal sacrificed and the aductor muscles (both ischemic and non-ischemic) collected. The kidneys were also collected and analyzed as internal control organs to demonstrate homogenous distribution of the microspheres throughout the blood stream of the animal. The harvested organs were weighed, digested with potassium hydroxide and the amount of fluorescent microspheres present quantified using a fluorescent spectrophotometer. This data together with the reference blood sample was used to calculate the absolute blood flow in the tissue, expressed in milliliter per minute per gram of tissue. The absolute blood flow measurements showed a dramatic improvement, nearing control levels in some cases, of the cell treated ischemic limb when compared to the normal non-ischemic limb (FIG. 2). The control vehicle only treated ischemic limb had approximately 60% of the blood flow compared to the healthy limb; whereas, the cell treated ischemic limb had approximately 85% of the blood flow compared to the healthy non-ischemic limb.

Figure 3:
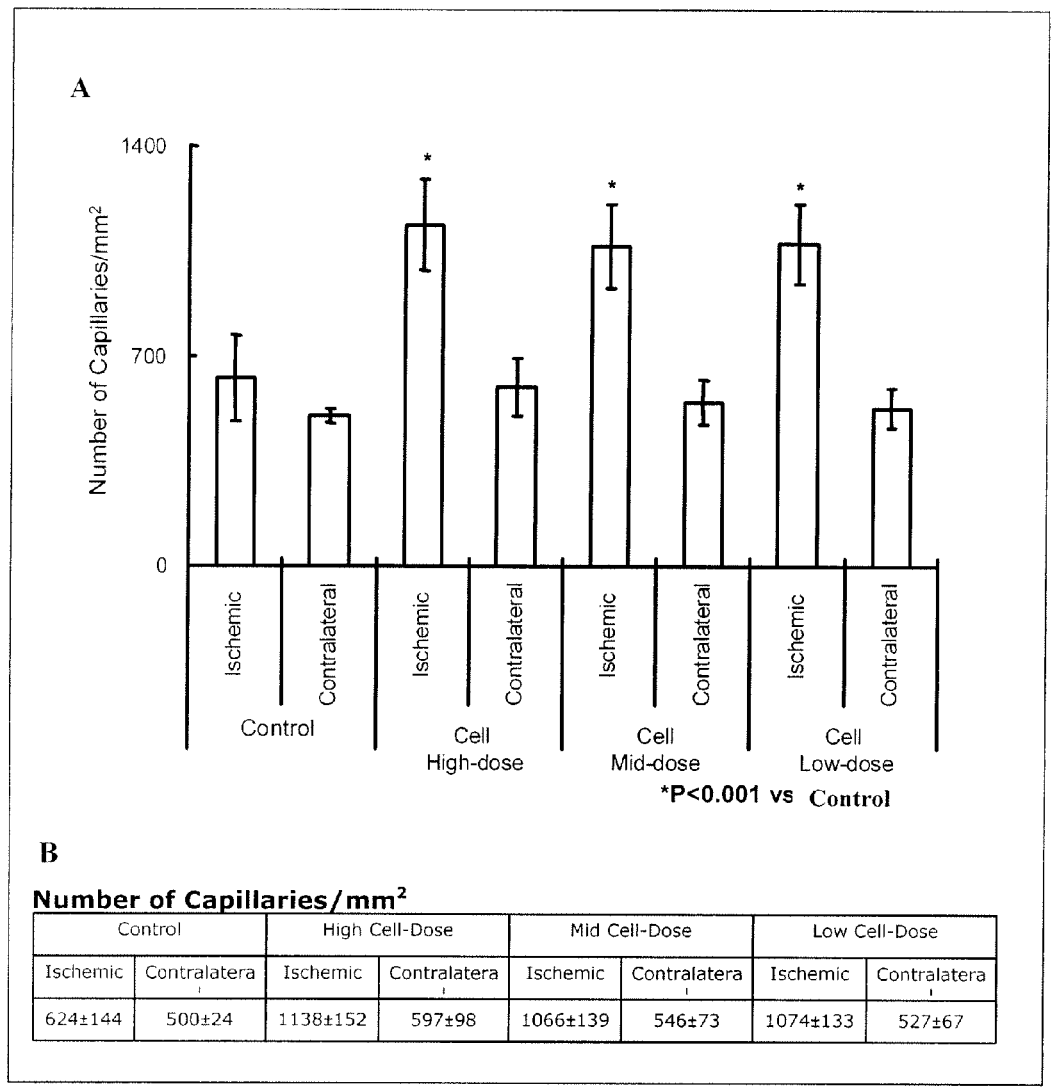
FIG. 3A) is a histogram showing the capillary density measured at 21 days in the ischemic and contralateral limb. A significant increase in the capillary density is observed in all of the cell treated ischemic limb groups compared to the vehicle treated ischemic limb group. B) Average capillary density data shown in A) in numerical table format.

The laser Doppler measurements and the blood flow measurements support that the ischemic limb has regained and has a sustained improvement resulting directly from the implantation of the cells into the adductor muscle at the point of artery ligation. To provide further evidence of the pro-angiogenic potential of the implanted human cells, the remaining five animals from each group were sacrificed at day 21 and the adductor muscles processed to paraffin for capillary density analysis by histology. Three 5 micron sections were collected from each ischemic and non-ischemic limb and stained for the endothelial cell marker isolectin B4. Isolectin B4 stained the capillaries within the muscle section. Capillary density was determined by manually counting the vessel density within 10 fields of view on each of the three sections processed. The cell treated ischemic limb has almost a two-fold increase in the capillary density compared to that of the control vehicle only treated ischemic limb (FIG. 3). The capillary density data conclusively demonstrates that the increase in blood flow observed in cell treated ischemic limb is achieved from an increased capillary density. Furthermore, the increased capillary density arises directly from the implantation of the cells as the control vehicle treated ischemic limb has little to no increased capillary density compared to non-ischemic limb.

Histopathology

Histology sections of the adductor muscle, surplus to the capillary density analysis, were further analyzed for adverse pathology and human cell survival. Hematoxylin and eosin (H&E) was carried out on a sample of all adductor muscle samples that included: ischemic, non-ischemic, control and cell treated muscle samples. No adverse histopathology was found within any of the cell treated groups, indicating the intramuscular injection of these cells is not toxic. Human cell survival within the paraffin fixed implanted murine adductor muscle samples was carried out using antibodies raised against human mitochondrial antigen (Millipore) and human specific antibodies raised against nestin (Millipore). These antibodies specifically recognize the implanted human cells and did not cross-react with the host murine antigens. Although an exhaustive sampling of the muscle tissue for human cell survival was not performed, human cell survival was demonstrated within only some of the implanted ischemic muscle samples but not all. As all animals with ischemic limbs treated with cells improved blood flow, long-term survival of the intramuscular implanted cells may not be an absolute requirement to achieve a therapeutic pro-angiogenic effect from the cell treatment.

Cell Formulation

The cells should be presented in a suspension that is compatible with patient administration. The cells used in the first experiment (FIGS. 1-3) were prepared from freshly harvested cultures and used within 24 hr. The formulation of these cells in Hypothermosol®-FRS is compatible with patient administration, however, in practice a 24 hr shelf-life of the cell product restricts the distribution to a large patient population. The cryopreserved cell suspension is formulated in the non-toxic Hypothermosol®-FRS solution but has the added advantages that it can be stored in a frozen state for an extended period of time and defrosted for direct patient administration with no further manipulation. It is important to note that the cryopreservation of the cells does not alter or change the biological activity of the cells to treat the ischemic muscle. In a direct comparative study between equivalent concentrations of fresh and cryopreserved cell suspensions, across three cell doses tested and four assays, the fresh and frozen cells gave statistically equivalent results in the treatment of the hind limb ischemia model as shown in Table 1.

TABLE 1

| Test Parameter[1] | CTX0E03 Cell Dose | | |
|---|---|---|---|
| | $3 \times 10^5$ | $3 \times 10^4$ | $3 \times 10^3$ |
| Doppler | ✓ | ✓ | X |
| Microsphere blood flow (ml/min/gm) | ✓ | ✓ | ✓ |
| PO$_2$ (mm/Hg) | ✓ | X | X |
| Capillary density | ✓ | ✓ | ✓ |

Clinical Outcome for Ischemia in Diabetes

Figure 4:
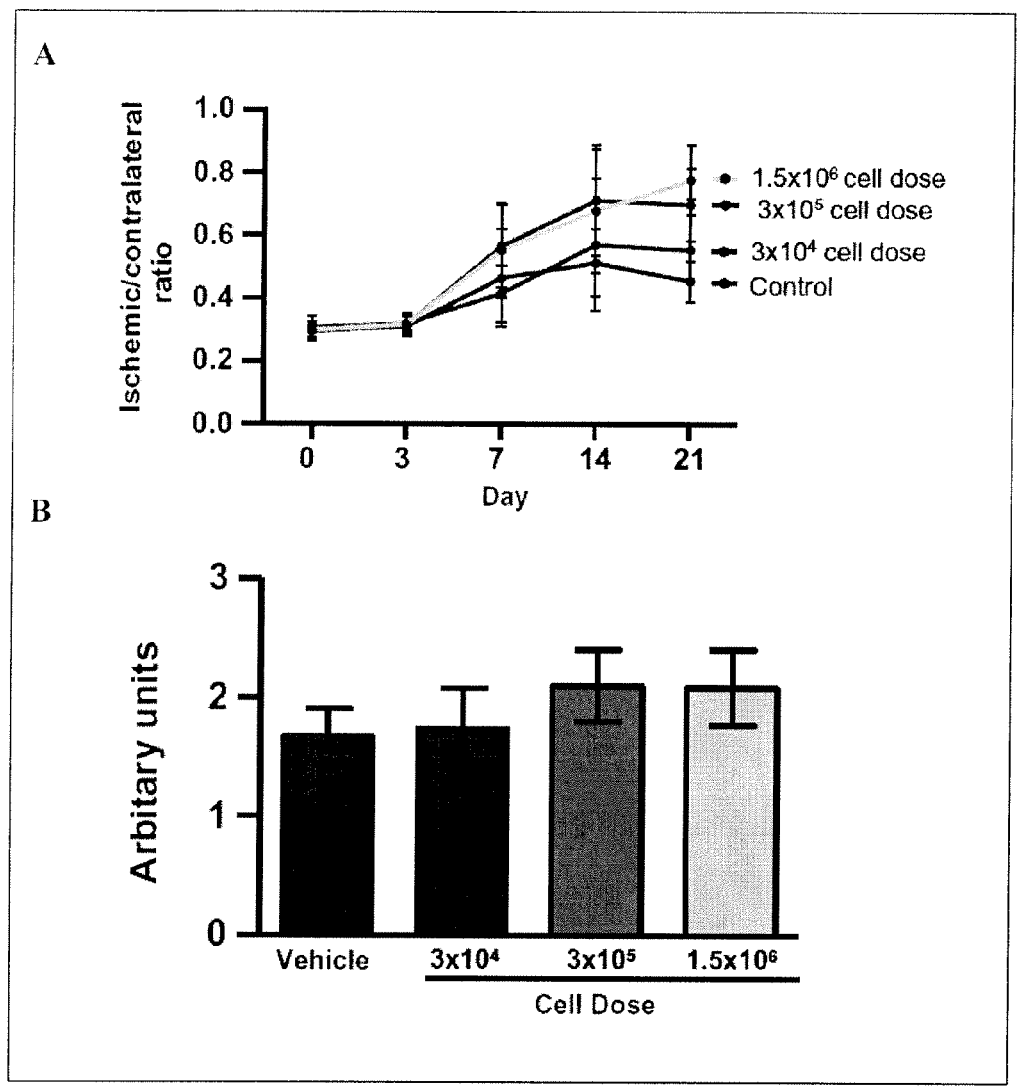
FIG. 4A) is a line graph showing that neural stem cell treated ischemic limb has an increased and sustained blood flow when compared to the vehicle only treated ischemic limb in an immune competent diabetic mouse model. Blood flow measurements where made using laser Doppler on days 0, 3, 7, 14 and 21. Data is expressed as average ratio of blood flow measured within the ischemic limb over the non-ischemic (contralateral) limb. B) is a histogram that graphs the area under each curve in that is shown in A). B) shows the overall improvement over the course of the study in the cell treated ischemic limb compared to vehicle only treated ischemic limb.
Figure 5:
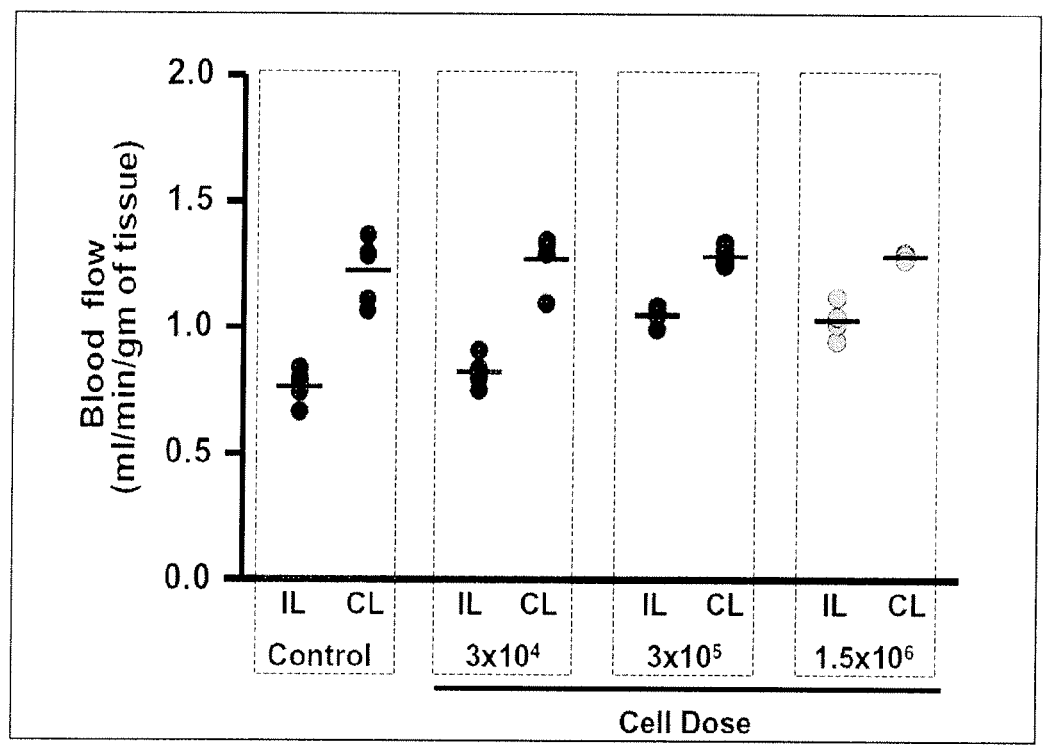
FIG. 5 is a scatter plot showing that neural stem cell treated limb muscle has an increase in blood flow (ml/min/gram of tissue) compared to the vehicle only treated ischemic limb muscle at 21 days in immune competent diabetic animals. Animals were perfused with fluorescent microspheres intravenously at the end of the 21 day study and the amount of fluorescent microspheres present in the ischemic limb (IL) and contralateral (CL) limb muscle tissue was measured. The amount of fluorescent microspheres present within the limb muscle tissue directly correlates with the amount of blood flow within the affected limb.
Figure 6:
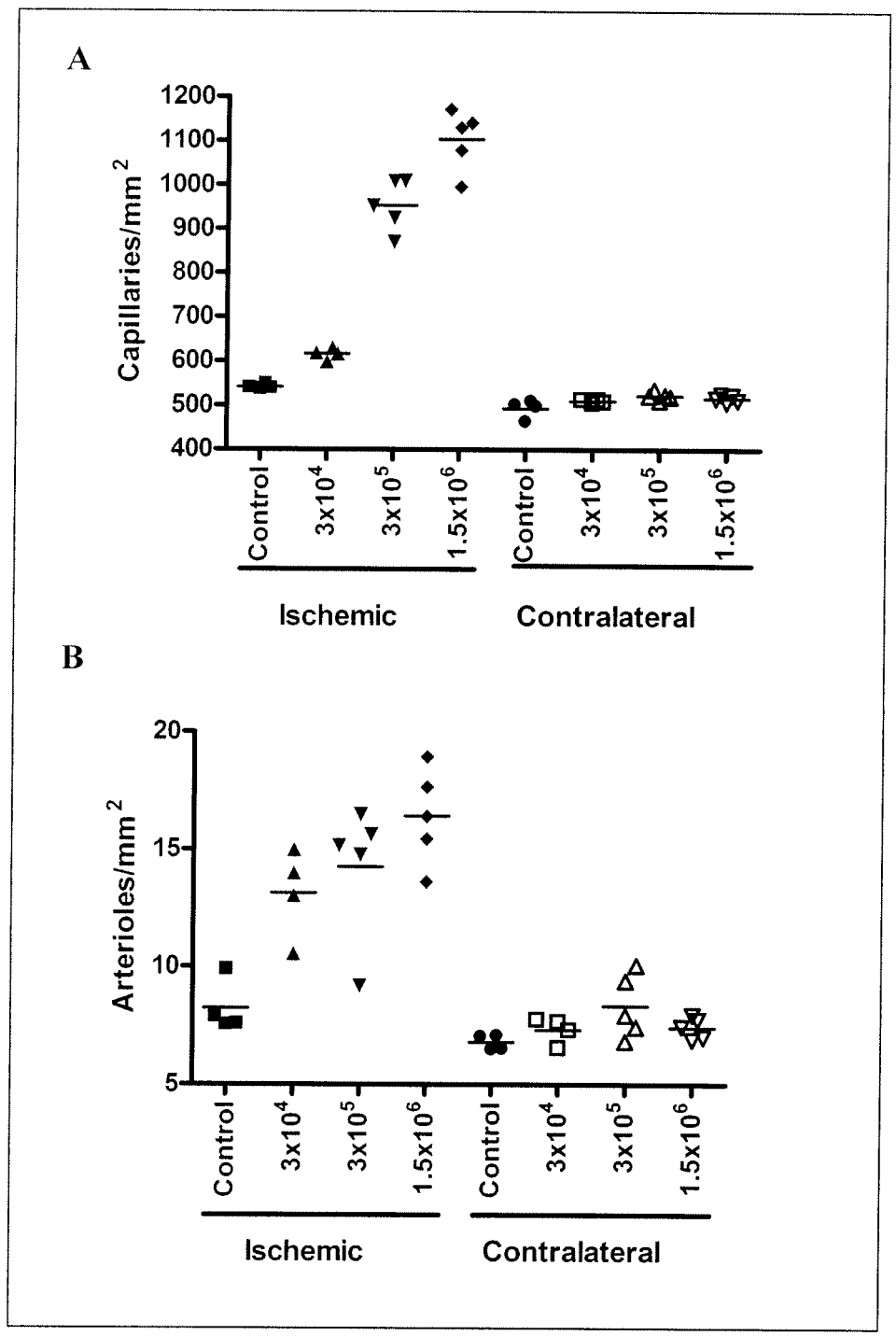
FIG. 6A) is a scatter plot showing the capillary density measured at 21 days in the ischemic and contralateral limb in an immune competent diabetic model. B) is a scatter plot showing the arteriole density measured at 21 days in the ischemic and contralateral limb in an immune competent diabetic model. A significant increase in the capillary density and arteriole density are observed in all of the cell treated diabetic ischemic limb groups compared to the vehicle treated diabetic ischemic limb group.

Diabetes is a significant contributing factor in the development of CLI. An immune competent diabetic model of hind limb ischemia was used to demonstrate that the cells are effective in treating limb ischemia in the presence of an underlying chronic disease. Diabetic animals treated with vehicle showed a reduced blood flow capacity compared to the control (non-diabetic) mice treated with vehicle. The lowest cell dose ($3 \times 10^4$ cells) produced no significant improvements and the two higher doses ($3 \times 10^5$ cells and $1.5 \times 10^6$ cells) showed markedly increased recovery in the blood flow to the ischemic limb, as measured by Doppler (FIG. 4), adductor muscle blood flow (FIG. 5) and capillary and arteriole density (FIG. 6).

Summary

The method presented in this invention describes neural stem cells suitable for the therapeutic treatment of limb ischemia, a form of peripheral arterial disease. The c-mycER technology is presented as a method to conditionally immortalise cell lines such that a sufficient number of cells can be made available to treat more than a limited number of patients with the said cell product. Furthermore, human neural stem cells provided a conclusive therapeutic pro-angiogenic effect in the murine hind-limb ischemia model, even in the presence of a chronic disease such as diabetes. The laser Doppler, fluorescent microsphere blood flow and capillary density analysis support and corroborate this conclusion. Indeed, the benefits of cell implantation were realized within days post-implantation and sustained for three-weeks. The cell doses presented in this method ($0.3 \times 10^6$ cells per animal to $3 \times 10^6$ cells per animal) had all achieved a therapeutic benefit in the analysis carried out.

The publications mentioned in the description are hereby incorporated herein by reference.

REFERENCES

Asahara T, Masuda H, Takahashi T, Kalka C, Pastore C, et al. 1999. Bone marrow origin of endothelial progenitor cells responsible for postnatal vasculogenesis in physiological and pathological neovascularization. *Circ Res* 85:221-8

Callum K, Bradbury A. 2000. ABC of arterial and venous disease: Acute limb ischemia. *Bmj* 320:764-7

Carpenter M K, Cui X, Hu Z Y, Jackson J, Sherman S et al. 1999. In Vitro Expansion of a Multipotent Population of Human Neural Progenitor Cells *Exp Neurol* 158:265-278

Conti L, Pollard S M, Gorba T, Reitano E, Toselli M, et al. 2005. Niche-independent symmetrical self-renewal of a mammalian tissue stem cell. PLoS Biol 3(9).

Gey D C, Lesho E P, Manngold J. 2004. Management of peripheral arterial disease. *Am Fam Physician* 69:525-32

Gray B H, Conte M S, Dake M D, Jaff M R, Kandarpa K, et al. 2008. Atherosclerotic Peripheral Vascular Disease Symposium II: lower-extremity revascularization: state of the art. *Circulation* 118:2864-72

Gu Y, Zhang J, Qi L. 2006. [Effective autologous bone marrow stem cell dosage for treatment of severe lower limb ischemia]. *Zhongguo Xiu Fu Chong Jian Wai Ke Za Zhi* 20:504-6

Liao L, Zhao R C. 2008. An overview of stem cell-based clinical trials in China. *Stem Cells Dev* 17:613-8

Littlewood T D, Hancock D C, Danielian P S, Parker M G, Evan G I. 1995. A modified oestrogen receptor ligand-binding domain as an improved switch for the regulation of heterologous proteins. *Nucleic Acids Res* 23:1686-90

Miljan E A, Hines S J, Pande P, Corteling R L, Hicks C, et al. 2008. Implantation of c-mycERTAM immortalized human mesencephalic derived clonal cell lines ameliorates behaviour dysfunction in a rat model of Parkinsons disease. *Stem Cells Dev*

Pollock K, Stroemer P, Patel S, Stevanato L, Hope A, et al. 2006. A conditionally immortal clonal stem cell line from human cortical neuroepithelium for the treatment of ischemic stroke. *Exp Neurol* 199:143-55

Reynolds B A and Weiss S. 1992. Generation of neurons and astrocytes from isolated cells of the adult mammalian central nervous system. *Science,* 255: 1707-1710

Stevanato L, Corteling R L, Stroemer P, Hope A, Heward J, Miljan E A, Sinden J D. 2009; c-MycERTAM transgene silencing in a genetically modified human neural stem cell line implanted into MCAo rodent brain. *BMC Neurosci.* 10:86

Tateishi-Yuyama E, Matsubara H, Murohara T, Ikeda U, Shintani S, et al. 2002. Therapeutic angiogenesis for patients with limb ischemia by autologous transplantation of bone-marrow cells: a pilot study and a randomised controlled trial. *Lancet* 360:427-35

Uchida N, Buck D W, He D, Reitsma M J, Masek M, et al. 2000. Direct isolation of human central nervous system stem cells. Proc Natl Acad Sci USA 97:14720-14725

Vescovi A L, Parati E A, Gritti A, Poulin P, Ferrario M. et al. 1999 Isolation and cloning of multipotential stem cells from the embryonic human CNS and establishment of transplantable human neural stem cell lines by epigenetic stimulation. *Exp. Neurol.* 156:71-83

The invention claimed is:

1. A method for treating peripheral arterial disease in a patient, comprising administering a therapeutic dose of neural stem cells to the patient, wherein the neural stem cells are those designated as CTX0E03.

2. The method according to claim 1, wherein the disease is limb ischemia or Buerger's disease.

3. The method according to claim 2, wherein the disease is critical limb ischemia.

4. The method according to claim 2, wherein the disease is acute limb ischemia.

5. The method according to claim 1, wherein the disease is associated with diabetes.

6. The method according to claim 1, wherein the neural stem cells are administered in a formulation, and wherein the formulation is in a form for intravenous or intramuscular delivery.

7. The method according to claim 1, wherein the cells are suspended in a composition comprising Trolox, $Na^+$, $K^+$, $Ca^{2+}$, $Mg^{2+}$, $Cl^-$, $H_2PO_4^-$, HEPES, lactobionate, sucrose, mannitol, glucose, dextran-40, adenosine and glutathione.

8. The method according to claim 1, wherein the patient is human.

* * * * *